United States Patent [19]

Loebel

[11] Patent Number: 4,708,957

[45] Date of Patent: Nov. 24, 1987

[54] INJECTION SOLUTION

[75] Inventor: Klaus D. Loebel, Hamburg, Fed. Rep. of Germany

[73] Assignee: Schering Aktiengesellschaft, Berlin and Bergkamen, Fed. Rep. of Germany

[21] Appl. No.: 770,449

[22] Filed: Aug. 29, 1985

[30] Foreign Application Priority Data

Aug. 29, 1984 [DE] Fed. Rep. of Germany ....... 3432112

[51] Int. Cl.$^4$ ............................................. A61K 31/52
[52] U.S. Cl. ..................................... 514/264; 514/826
[58] Field of Search ................................ 514/264, 826

[56] References Cited

U.S. PATENT DOCUMENTS 3,900,474  8/1975  Ginger et al. .................. 514/826 X
3,928,609  12/1975  Behrakis .............................. 514/264

Primary Examiner—Leonard Schenkman
Attorney, Agent, or Firm—Millen & White

[57] ABSTRACT

An aqueous injection solution contains 1–25% by weight of 2-hydroxy-N,N,N-trimethyl-ethanaminium salt of 3,7-dihydro-1,3-dimethyl-1H-purine-2,6-dione (1:1) and, based on this salt, 5–8% by weight of propionic acid.

18 Claims, No Drawings

INJECTION SOLUTION

BACKGROUND OF THE INVENTION

As is known, the 2-hydroxy-N,N,N-trimethylethanaminium salt of 3,7-dihydro- 1,3-dimethyl-1H-purine-2,6-dione (1 : 1) (choline theophyllinate) is a pharmacologically effective compound contained as the active ingredient in broncholytically active medicines ("Rote Liste 1980" [Red List 1980] Editio Cantor Publishers, Aulendorf, Wuerttemberg DT, No. 27 042). This salt of theophylline has the advantage over other salts of this compound, for example, theophylline ethylenediamine (=aminophylline), of being more compatible. (Arzneim. Forsch., 31 : 1503 et seq., 1981, and 32 : 409 et seq., 1982). The preparations containing choline theophyllinate are administered orally. As a consequence, the active agent concentration in the blood plasma reaches its maximum only after about two hours (Brit. J. Pharmacol. 3 : 194-196, 1976), which is a disadvantage especially in the treatment of grave, spasmodic conditions. There is thus a need for injection media containing this active ingredient.

Aqueous solutions of choline theophyllinate are unstable and accordingly unsuitable for injection media. An attempt at stabilizing these solutions by adding acids or antioxidants customarily employed in galenic pharmacy (formic acid, acetic acid, phosphoric acid, benzoic acid, glutaric acid, adipic acid, sorbic acid, malic acid, tartaric acid, ascorbic acid, citric acid, etc.) results in precipitation of the choline theophyllinate, or solutions are obtained that are likewise unstable, discoloring, and unsterilizable.

SUMMARY OF THE INVENTION

It is an object of this invention to provide such injection solution.

Upon further study of the specification and appended claims, further objects and advantages of this invention will become apparent to those skilled in the art.

It has now been found that stable aqueous solutions of choline theophyllinate are suprisingly obtained by adding to this solution, based on the amount of salt, 5–8% by weight, preferably 6–7% by weight and especially 6.5–6.8% by weight of propionic acid. The resultant solutions exhibit a pH of about 9–10 —preferably 9.4–9.8. They can be prepared fully conventionally from the usual starting materials and dispensed as usual into ampoules or the like and sterilized.

DETAILED DISCUSSION

In these aqueous injection solutions, the concentration of choline theophyllinate is 1–25, preferably 2–20, and especially 3–15% by weight.

The aqueous injection solutions of this invention can be utilized, inter alia, for the treatment in mammals including humans of acute and grave spasmodic conditions of the bronchial passages in chronic bronchitis, pulmonary emphysema, or bronchial asthma—particularly in status asthmaticus. The initial dose administered should preferably be 5–10 mg/kg and especially 7–9 mg/kg of body weight; the daily dose administered should range approximately within the limits of 15–40 mg/kg and particularly in the limits of 19–31 mg/kg of body weight.

The injection medium of this invention can be administered analogously to other injection solutions.

Conventional additives normally included in such injection solutions (see for instance: Lawrence Trissel Handbook on Injectable Drugs, Am. Soc. of Hospital Pharmacists Application Services, Washington, D.C. 1977) can, of course, also be included in the injection solution of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1 10.00 liters of an injection solution is prepared from 300.00 g of choline theophyllinate
20.00 g of propionic acid and
9,730.00 g of double-distilled water This solution is filtered under sterile conditions and dispensed, under sterile conditions, into ampoules of 10.00 ml each.

EXAMPLE 2 1.00 liter of an injection solution is prepared from 150.00 g of choline theophyllinate
10.00 g of propionic acid and
875.00 g of double-distilled water This solution is filtered under sterile conditions and dispensed into ampoules of 1.00 ml each.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aqueous injectable solution comprising a broncholytically active amount of the 2-hydroxy-N,N,N-trimethyl-ethanaminium salt of 3,7-dihydro- 1,3-dimethyl-1H-purine-2,6-dione (1:1) and 5–8% by weight of propionic acid based on the amount of salt.

2. An injection solution of claim 1 wherein the amount of salt is 1–25% by weight.

3. An injection solution of claim 1 wherein the amount of salt is 2–20% by weight.

4. An injection solution of claim 1 wherein the amount of salt is 3–15% by weight.

5. An injection solution of claim 2, wherein the amount of propionic acid is 6–7% by weight.

6. An injection solution of claim 3, wherein the amount of propionic acid is 6–7% by weight.

7. An injection solution of claim 4, wherein the amount of propionic acid is 6–7% by weight.

8. An injection solution of claim 2, wherein the amount of propionic acid is 6.5–6.8% by weight.

9. An injection solution of claim 3, wherein the amount of propionic acid is 6.5–6.8% by weight.

10. An injection solution of claim 4, wherein the amount of propionic acid is 6.5–6.8% by weight.

11. An injection solution of claim 2 having a pH of about 9–10.

12. An injection solution of claim 10 having a pH of about 9–10.

13. A method of treating a condition treatable with the 2-hydroxy-N,N,N-trimethyl-ethanaminium salt of 3,7-dihydro-1,3-dimethyl-1H-purine-2,6-dione (1:1) comprising injecting a patient with a therapeutic amount of an aqueous solution of claim 1.

14. A method of treating a condition treatable with the 2-hydroxy-N,N,N-trimethyl-ethanaminium salt of 3,7-dihydro-1,3-dimethyl-1H-purine-2,6-dione (1:1) comprising injecting a patient with a therapeutic amount of an aqueous solution of claim 2.

15. A method of claim 13 wherein the patient is suffering from an acute or grave spasmodic condition.

16. A method of claim 15 wherein the initial dose is 5–10 mg/kg and the subsequent daily dose is 15–40 mg/kg.

17. A method of claim 16 wherein the initial dose is 7–9 mg/kg and the subsequent daily dose is 19–31 mg/kg.

18. A method of claim 15 wherein the patient is suffering from chronic bronchitis, pulmonary emphysema, or bronchial asthma.

* * * * *